United States Patent [19]

Schmolka

[11] Patent Number: 4,678,664

[45] Date of Patent: Jul. 7, 1987

[54] MINERAL OIL GELS

[75] Inventor: Irving R. Schmolka, Grosse Ile, Mich.

[73] Assignee: BASF Corporation, Wyandotte, Mich.

[21] Appl. No.: 430,175

[22] Filed: Sep. 30, 1982

[51] Int. Cl.$^4$ .......................... A61K 7/32; A61K 7/34; A61K 7/36; A61K 7/38

[52] U.S. Cl. .............................. 424/65; 424/DIG. 4; 424/DIG. 10; 424/66; 424/67; 424/68; 424/145; 514/563

[58] Field of Search ...................... 424/59, 13, 65, 70, 424/170, 168, 65, 68; 252/316; 568/624

[56] References Cited

U.S. PATENT DOCUMENTS

| | | | |
|---|---|---|---|
| 2,828,345 | 3/1958 | Spriggs | 568/624 |
| 4,042,525 | 8/1977 | Ackermann et al. | 568/624 |
| 4,326,977 | 4/1982 | Schmolka | 252/174.21 |
| 4,341,799 | 7/1982 | Good | 424/365 |
| 4,360,451 | 11/1982 | Schmolka | 424/78 |

*Primary Examiner*—Dale R. Ore
*Attorney, Agent, or Firm*—Joseph D. Michaels; Bernhard R. Swick

[57] ABSTRACT

This invention relates to a gel composition comprising water, mineral oil and two polyoxyethylene-polyoxybutylene block copolymers designated copolymer A and copolymer B wherein said block copolymers are cogeneric mixtures of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms wherein copolymer A has a molecular weight of the polyoxybutylene portion of at least about 1800 and the polyoxyethylene portions contribute from about 60 to 80 percent by weight of the compound and copolymer B has a polyoxybutylene portion with a molecular weight of at least about 600 and the polyoxyethylene portion contributes from about 20 to 40 percent by weight of the compound.

10 Claims, No Drawings

MINERAL OIL GELS

BACKGROUND OF THE INVENTION

1. Field of the Invention

This invention relates to aqueous gels prepared from nonionic surfactants in mineral oil. These gels are particularly useful in the formation of topically applied cosmetic and pharmaceutical compositions.

2. Description of Earlier Work and Discoveries

U.S. Pat. No. 3,740,421 relates to polyoxyethylene-polyoxypropylene aqueous gels. Polyoxyethylene-polyoxypropylene block copolymers form gels within certain specified ranges of compositions with water. U.S. Pat. No. 3,639,574 relates to hydrogen peroxide gels prepared employing certain polyoxyethylene-polyoxypropylene block copolymers as gelling agents. U.S. Pat. No. 3,579,465 relates to polyoxyethylene-polyoxypropylene adducts of ethylene diamine which, within specified limits form aqueous gels. These gels are prepared by dissolving the block copolymer in water at a temperature between 1° C. and 10° C. and thereafter warming to about 30° C. to form the gel.

Among the problems of these gel compositions is that they liquify at temperatures below about 30° C. Therefore, they cannot be stored as gels in a refrigerator or freezer or in a cold room, below normal room temperature.

U.S. Pat. No. 2,828,345 discloses emulsifying mineral oil in water with a series of butylene oxide-ethylene oxide polymers having a molecular weight of the butylene oxide groups of 1100 to 1400 and having oxyethylene weight percents ranging from 40 to 80. U.S. Pat. No. 4,040,857 discloses compositions exemplified by thixotropic emulsions employing as emulsifiers copolymers of butylene oxide, propylene oxide and ethylene oxide. All three components are essential in this patent.

Copending U.S. patent application, Ser. No. 287,203, filed July 27, 1981, discloses a polyoxybutylene-polyoxyethylene aqueous gel. There is no mention therein of mineral oil. In the prior art the preparation of stable homogeneous gel systems of mineral oil and water generally requires complex processes and apparatuses such as homogenizers.

SUMMARY OF THE INVENTION

It has now been found that stable, homogeneous mineral oil gels can be prepared with polyoxybutylene-polyoxyethylene block copolymers which surprisingly do not require complex processing or apparatuses such as homogenizers. Also, they do not liquify below about 30° C. More specifically, the instant invention comprises the use of a combination of two such polyoxybutylene-polyoxyethylene block copolymers, namely, such a copolymer wherein the total molecular weight of the polyoxybutylene groups is at least about 1800 and preferably is from about 1800 to 6000 and has a percent of the oxyethylene groups of from about 60 to 90, designated copolymer A in combination with such a copolymer having a molecular weight of the polyoxybutylene groups of at least about 600 and preferably from about 600 to 6000 and containing about 20 to 40 percent oxyethylene groups, designated copolymer B.

The overall composition comprises from about 50 to 85 percent by weight water; up to about 20, preferably from about 5 to 10 percent by weight mineral oil, from about 10 to 25 percent by weight of copolymer A and about 2 to 10 percent by weight of copolymer B.

DESCRIPTION OF THE PREFERRED EMBODIMENTS

Each block copolymer is a cogeneric mixture of conjugated polyoxybutylene-polyoxyethylene compounds containing in their structure hydrophobic oxybutylene groups; hydrophilic oxyethylene groups and an organic radical derived from an organic compound containing a plurality of reactive hydrogen atoms. This is preferably a water-soluble organic compound containing a plurality of reactive hydrogen atoms and 2 to 12 carbon atoms. The compounds are characterized in that the oxybutylene groups are present in polyoxybutylene chains that are attached to the organic radical at the site of a reactive hydrogen atom thereby principally constituting a polyoxybutylene polymer. The oxyethylene groups are attached to the polyoxybutylene polymer in polyoxyethylene chains.

The hydrophobic oxybutylene chains may optionally, but advantageously, contain small amounts of oxyethylene and/or oxypropylene groups which may partially replace the oxybutylene groups to provide a ratio in the predominantly oxybutylene hydrophobic chains of oxyethylene and/or oxypropylene groups to oxybutylene groups of from about 1:20 to about 1:3. Similarly, the hydrophilic oxyethylene chains may also optionally, but advantageously, contain small amounts of oxyalkylene groups such as oxypropylene and oxybutylene groups which may replace the oxyethylene groups whereby the ratio of oxypropylene and/or oxybutylene groups to oxyethylene groups in the hydrophilic chains may range from about 1:20 to 1:4, and preferably about 1:20 to 1:9.

It is to be understood that the expression polyoxyethylene-polyoxybutylene block copolymer includes such amounts of oxypropylene and/or oxyethylene groups in the hydrophobic polyoxybutylene chains and such amounts of oxypropylene and/or oxybutylene groups in the hydrophilic polyoxyethylene chains.

In copolymer A, the average molecular weight of the polyoxybutylene groups in the mixture is at least about 1800 and preferably from about 1800 to 6000 and the oxyethylene groups constitute about 60 to 80 percent by weight of the compound. In copolymer B, the average molecular weight of the polyoxybutylene groups in the mixture is at least about 600 and preferably from about 600 to 6000 and the oxyethylene groups constitute 20 to 40 percent by weight of the compound.

The polyoxybutylene-polyoxyethylene copolymers are prepared by first condensing butylene oxide with an organic compound containing a plurality of reactive hydrogen atoms to prepare a polyoxybutylene polymer of the desired molecular weight and subsequently condensing ethylene oxide therewith. The polyoxybutylene polymer which is an intermediate in the preparation of the compounds of use in this invention has the following structure:

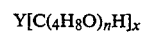

$$Y[C(_4H_8O)_nH]_x$$

wherein Y is the residue of a water-soluble organic compound containing therein active hydrogen atoms; n is an integer; x is an integer greater than 1; the values of n and x are such that the molecular weight of this intermediate for the copolymer A is at least about 1800 and preferably from about 1800 to 6000 and for the copolymer B it is at least about 600 and preferably from about 600 to 6000. In lieu of butylene oxide, other four carbon ethers, such as methyloxetane, tetrahydrofuran and isobutylene oxide may be used.

The preferred compounds of use in this invention are prepared by condensing ethylene oxide in an amount between about 60 and 80 percent by weight of the resultant compound with the polyoxybutylene polymer for copolymer A and about 20 and 40 percent by weight ethylene oxide for copolymer B. These compounds have the following formula:

$$Y[(C_4H_8O)_n(C_2H_4O)_mH]_x \quad (I)$$

wherein Y, n and x are as defined above and m has a value such that the oxyethylene groups constitute about 60 to 80 percent by weight of the compound for copolymer A and 20 to 40 percent by weight for copolymer B. When ethylene oxide is condensed with a polyoxybutylene glycol derived from a butanediol initiator, the resulting compounds have the following structure:

$$HO(C_2H_4O)_{m'}(C_4H_8O)_n(C_2H_4O)_mH \quad (II)$$

where n is defined as previously set forth; and m' and m have a value such that the oxyethylene groups constitute about 60 to 80 percent by weight of the compound for copolymer A and 20 to 40 percent by weight for copolymer B. The hydrophilic portion of the polyoxyalkylene compounds may be supplied in whole or in part by other polyoxyalkylene chains in lieu of the polyoxyalkylene chains set forth in the above formula. Any polyoxyalkylene chain may be used provided that the oxygen/carbon ratio contained therein is at least 0.5.

Alternatively, copolymer B may correspond to the formula:

$$Y[(C_2H_4O)_m(C_4H_8O)_nH]_x \quad (III)$$

wherein Y, n, m and x have values as set forth above. This copolymer is prepared in substantially the same way as the copolymer of formula I with the exception that a polyoxyethylene polymer is prepared having the structure:

$$Y[C_2H_4O)_nH]_x$$

which is then condensed with butylene oxide. Preferred compounds of this type have the following structure:

$$HO(C_4H_8O)_n(C_2H_4O)_m(C_4H_8O)_{n'}H \quad (IV)$$

wherein m is defined as previously set forth and n'+n have a value such that the oxyethylene groups constitute 20 to 40 percent by weight of the compound. Mixtures of copolymers defined by formula III or IV with copolymers defined by formula I or II may be employed as copolymer B.

Examples of a water-soluble organic compound containing therein x active hydrogen atoms, the residue of which is Y, are the initiators which may include water; diols such as propane diol, butanediol, and ethylene glycol, triols such as glycerol, tetrols such as pentaerythritol as well as initiators containing more than 4 hydroxyl groups such as hexitol or sucrose. Also amines and other low molecular weight water-soluble compounds having two or more active hydrogen atoms such as ethylene diamine or diethylenetriamine may be used as the initiator. Butane diol, preferably 1,4-butane diol, is preferred in formula I, and ethylene glycol is preferred in formula III.

A more detailed disclosure of the preparation of the polyoxybutylene-polyoxyethylene copolymers can be found, for instance, in U.S. Pat. Nos. 2,828,345, 4,326,977, British Pat. No. 722,746 and *Block and Graft Copolymerization,* vol. 2, edited by R. J. Ceresa, pages 68 and 69, John Wiley and Sons.

By the expression "mineral oil" is meant a clear colorless nearly odorless and tasteless liquid obtained from the distillation of petroleum. It is also called white oil, white mineral oil, liquid petrolatum, liquid paraffin or white paraffin oil. Mineral oil is a highly refined oily liquid which is commercially available as a technical grade, as a NF (national formulary) grade and as a USP grade. The specific gravity of mineral oil generally lies between 0.860 and 0.905 gm/cc and its minimum boiling point is 360° C. The number after the commercial name is indicative of the SUS viscosity at 100° F. They are usually free of aromatics and unsaturated compounds.

As used herein, the term "gel" is defined as a solid or semi-solid colloid containing considerable quantities of water. The particles in the gel are linked in a coherent mesh work which imobilizes the water. The colloidal solution with water as a dispersion medium is often called a "hydrosol." The gels within the scope of the present invention are more specifically "ringing" gels and may be described as gels that have a firm jelly-like consistency; that is, by tapping the gel lightly, it will vibrate and return to its original configuration.

The gels of the invention may be prepared by (1) dissolving the polyoxybutylene-polyoxyethylene block copolymer A in water at 60° C. to 80° C., (2) adding a 50/50 blend of the polyoxybutylene-polyoxyethylene block copolymer B and mineral oil with gentle mixing, while cooling to room temperature until it sets up into a gel. The percentage by weight based on the total weight of the composition for the A polyol is about 10 to 25, for the B polyol, is from about 2 to 10, the percent of the mineral oil is from about 1 to 20 and the water is about 50 to 85. Within the scope of this invention, the four components may be mixed together in any order, the above being merely one preferred order of mixing. When a homogeneous solution is obtained, upon cooling to about 30° C., an opaque homogeneous ringing gel is obtained. When ingredients other than water and the polyoxybutylene-polyoxyethylene block copolymers of this invention are used, the other ingredients may be added during either step 1 or step 2 above or even after step 3. Upon cooling, a ringing gel is obtained.

The aqueous gels of the invention may include various other additives in amount of about 1 to 25 percent by weight. For example, those which are normally used in cosmetic products for the skin such as perfumes, colors, phosphate esters, organic sulfates and sulfonates, other emollients, such as lanolin and its derivatives, preservatives, other solvents, etc., the aqueous gels of this invention may include a deodorant or antiperspirant such as those based on oxyquinolin salts, zinc oxide, etc., and astringents, such as aluminum chlorohydrate; and an antiseptic such as hexachloro dihydroxydiphenyl methane as well as propionic acid salts, lactic acid, and boric acid. The compositions may also include various anti-psoriasis drugs, vitamins, and other drugs, any or all of which can be included in these formulations. Also, the gels of this invention may contain materials for treating planters' warts, such as cantharidin, ingredients for treating athlete's foot such as undecylenic acid; materials for treating other microorganisms and insect repellants such as N,N-diethyltoluamide. To those skilled in the cosmetic and pharmaceutical sciences, it will become apparent that these gels may be used in shampoos, in skin creams, and other skin and hair products.

The following examples will further illustrate the various aspects of the invention. Where not otherwise specified throughout this specification and claims, temperatures are in degrees centigrade, and parts, percentages and proportions are by weight.

Illustrative block copolymers both type A and type B which may be employed in the preparation of the gels of the present invention, including the molecular weight of the polyoxybutylene hydrophobe, the weight percent of the polyoxyethylene hydrophile as well as the theoretical total molecular weight of the polymer are presented in Table I below. These block copolymers are made from a polyoxybutylene hydrophobe prepared by condensing 1,2-butylene oxide with 1,4-butane diol.

TABLE I

| Block Copolymer Type | No. | Molecular Weight of Hydrophobe (Avg.) | Weight Percent of Hydrophile (Avg.) | Approximate Total Molecular Weight of Copolymer |
|---|---|---|---|---|
| A | 1 | 1800 | 70 | 6000 |
| A | 2 | 1800 | 80 | 9000 |
| A | 3 | 2400 | 60 | 6000 |
| A | 4 | 2400 | 80 | 12,000 |
| A | 5 | 3000 | 60 | 7500 |
| A | 6 | 3000 | 70 | 10,000 |
| A | 7 | 3000 | 80 | 15,000 |
| B | 8 | 600 | 20 | 750 |
| B | 9 | 1200 | 20 | 1500 |
| B | 10 | 1800 | 20 | 2250 |
| B | 11 | 1800 | 40 | 3000 |
| B | 12 | 2400 | 20 | 3000 |
| B | 13 | 2400 | 40 | 4000 |
| B | 14 | 3000 | 20 | 3750 |
| B | 15 | 3000 | 40 | 5000 |

EXAMPLE 1

Block copolymer 7 in amount of 18 parts was added to 78 parts of distilled water at 80° C. after which a blend of 2 parts block copolymer 8 and 2 parts mineral oil, based on the total weight of the composition, was added followed by mixing slowly and cooling down below 60° C. whereupon an opaque gel was formed.

EXAMPLE 2

The procedure of Example 1 was repeated wherein 15 parts of block copolymer 7 and 81 parts of water were employed. The balance of the process was the same. However, upon cooling, the gel point of the opaque gel was 51° C.

EXAMPLE 3

The procedure of Example 1 was followed with the exception that 13 parts of copolymer 7 and 83 parts of water were employed and in lieu of a 1:1 mixture of mineral oil and copolymer 8, 2 parts of mineral oil were added first and then the two parts of copolymer 8. An opaque gel formed upon cooling.

EXAMPLE 4

The procedure of Example 3 was followed with the exception that 15 parts of copolymer 7, 79 parts of distilled water and 4 parts of copolymer 8 were employed. The opaque gel formed on cooling below 70° C.

EXAMPLE 5

The general procedure of Example 1 was followed with the exception that 13 parts of copolymer 7 was employed with 83 parts of the distilled water. The product was an opaque gel with a gel point of 42° C. It was placed in a 50° C. oven over night and then in an 80° C. oven for 30 minutes. The product liquified but did not separate, showing its stability. Upon recooling to room temperature, the gel reformed.

EXAMPLE 6

Block copolymer 7 in an amount of 12 parts was added to 68 parts of water and the mixture heated and stirred at 80° C. until homogeneous. Twenty parts of a 50/50 by weight blend of copolymer 8 and mineral oil were then added with gentle mixing to the hot solution. Upon cooling to room temperature, an opaque gel formed with a gel point of greater than 60° C.

EXAMPLES 7-10

Gels were prepared using the general procedure of Example 1. The block copolymers used, percent by weight of each block copolymer, distilled water and mineral oil are shown below in Table II. At room temperature all samples were white opaque gels.

TABLE II

| Example No. | | Weight Percent |
|---|---|---|
| 7 | Copolymer 6 | 20 |
|  | Distilled H$_2$O | 70 |
|  | Copolymer 14 | 5 |
|  | Mineral Oil | 5 |
| 8 | Copolymer 7 | 18 |
|  | Distilled H$_2$O | 64 |
|  | Copolymer 14 | 10 |
|  | Mineral Oil | 8 |
| 9 | Copolymer 4 | 22 |
|  | Distilled H$_2$O | 70 |
|  | Copolymer 10 | 3 |
|  | Mineral Oil | 5 |
| 10 | Copolymer 2 | 25 |
|  | Distilled H$_2$O | 70 |
|  | Copolymer 9 | 2 |
|  | Mineral Oil | 3 |

Example 11-15 show practical applications of the ringing gels. The gel pereparation procedure used is as generally described in Example 1. The other ingredients are added to the solution while hot. Upon obtaining a solution and cooling to about 30° C., a ringing gel is obtained.

EXAMPLE 11

A vaginal gel is prepared from the following formulation:

| Component | Parts by Weight |
|---|---|
| Calcium propionate | 3 |
| Sodium propionate | 3 |
| Mineral oil USP | 5 |
| Block copolymer 7 | 18 |
| Boric acid | 3 |
| Block copolymer 8 | 2 |
| Water | 66 |

EXAMPLE 12

A gel composition is prepared for treating planters' warts. A cantharidin is suspended in the gel matrix of the following formulation:

| Component | Parts by Weight |
|---|---|
| Cantharidin | 1.8 |
| Propylene glycol | 4 |
| Block copolymer 7 | 18 |
| Block copolymer 8 | 2 |
| Mineral oil | 2 |
| Water | 72.2 |

EXAMPLE 13

An insect repllellent gel is formed from the following formulation:

| Component | Parts by Weight |
|---|---|
| Block copolymer 7 | 15 |
| Block copolymer 8 | 2 |
| Mineral oil | 2 |
| Isopropylalcohol | 5 |
| N,N—diethyltoluamide | 5 |
| Water | 71 |
| Preservative | q.s. |

EXAMPLE 14

An athlete's foot gel is prepared from the following formulation:

| Component | Parts by Weight |
|---|---|
| Block copolymer 4 | 12 |
| Block copolymer 10 | 3 |
| Mineral oil | 5 |
| Undecylenic acid | 3 |
| Isopropyl alcohol | 7 |
| Water | 70 |

The embodiments of the invention in which an exclusive privilege or property is claimed are defined as follows:

1. In a mineral oil gel composition the improvement for achieving a stable, homogeneous gel which does not require high speed mixing, wherein said composition consists essentially of by weight about 1 to 20 percent mineral oil, about 10 to 25 percent of a polyoxyethylene-polyoxybutylene block copolymer designated as copolymer A, about 2 to 10 percent of a polyoxyethylene-polyoxybutylene block copolymer designated as copolymer B wherein said block copolymers are cogeneric mixtures of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms wherein copolymer A has a molecular weight of the polyoxybutylene portion of at least about 1800 and the polyoxyethylene portions contribute from about 60 to 80 percent by weight of the compound and copolymer B has a polyoxybutylene portion with a molecular weight of at least about 600 and the polyoxyethylene portion contributes from about 20 to 40 percent by weight of the compound, 0 to about 25 percent of other additives, balance water.

2. The gel composition of claim 1 wherein the maximum molecular weight of the polyoxybutylene portion of copolymer A and copolymer B is about 6000.

3. The composition of claim 2 wherein said polyoxyethylene-polyoxybutylene block copolymer A has the formula:

$$Y[(C_4H_8O)_n(C_2H_4O)_mH]_x$$

and copolymer B has the formula $$Y[(C_4H_8O)_n(C_2H_4O)_mH]_x$$

or $$Y[(C_2H_4O)_m(C_4H_8O)_nH]_x$$

or mixtures thereof wherein Y is the residue of a water-soluble organic compound containing therein x active hydrogen atoms and wherein n, m, and x are integers such that copolymer A consists of 60 to 80 percent by weight of polyoxyethylene groups and the molecular weight of the polyoxybutylene groups is about 1800 to 6000 and wherein copolymer B consists of 20 to 40 percent by weight polyoxyethylene groups and the molecular weight of the polyoxybutylene groups is about 600 to 6000.

4. The composition of claim 3 consisting essentially of about 10 to 25 percent copolymer A, 2 to 10 percent by weight copolymer B and up to 20 percent by weight mineral oil balance water and other additives.

5. The composition of claim 4 wherein said additives total 2 to 25 percent by weight of the composition and are selected from the group consisting of colors; preservatives, solvents, deodorants, antiperspirants, astringents, antiseptics, antipsoriasis drugs, vitamins, insect repellants; materials for treating planters' warts, ingredients for treating athlete's foot and for treating other harmful microorganisms.

6. The composition of claim 4 wherein said additives total 2 to 25 percent by weight of the composition and are selected from the group consisting of phosphate esters, organic sulfates and sulfonates, lanolin and its derivatives, oxyquinolin salts, zinc oxide, aluminum chlorohydrate; hexachlorodihydroxydiphenyl methane, cantharidin, undecylenic acid; N,N-diethyltoluamide, propionic acid salts, lactic acid and boric acid.

7. The composition of claim 1 wherein copolymer A has the formula:

$$HO(C_2H_4O)_m(C_4H_8O)_n(C_2H_4O)_{m'}H$$

and copolymer B is selected from the group consisting of:

$$HO(C_2H_4O)_m(C_4H_8O)_n(C_2H_4O)_{m'}H$$

and $$HO(C_4H_8O)_n(C_2H_4O)_m(C_4H_8O)_{n'}H$$

and mixtures thereof wherein m, n, m' and n' are integers such that copolymer A consists of 60 to 80 percent by weight polyoxyethylene groups and has a molecular weight of the polyoxybutylene groups of about 1800 to 6000 and copolymer B consists of 20 to 40 percent by weight polyoxyethylene groups and the molecular weight of the polyoxybutylene groups is about 600 to 6000.

8. The composition of claim 7 consisting essentially of by weight about 10 to 25 percent copolymer A, 2 to 10 percent copolymer B and up to 20 percent mineral oil balance water and other additives.

9. The composition of claim 8 wherein said additives total 2 to 25 percent by weight of the composition and are selected from the group consisting of: perfumes, colors, emollients, preservatives, solvents, deodorants, antiperspirants, astringents, antiseptics, anti-psoriasis drugs, insect repellants; materials for treating planters' warts, ingredients for treating athlete's foot and for treating other harmful microorganisms.

10. The composition of claim 8 wherein said additives total 2 to 25 percent by weight of the composition and are selected from the group consisting of: phosphate esters, organic sulfates and sulfonates, lanolin and its derivatives, oxyquinolin salts, zinc oxide, aluminum chlorohydrate; hexachloro dihydroxydiphenyl methane, cantharidin, undecylenic acid; and N,N-diethyltoluamide, propionic acid salts, lactic acid and boric acid.

* * * * *